US012611189B2

(12) United States Patent
Ikeda et al.

(10) Patent No.: US 12,611,189 B2
(45) Date of Patent: Apr. 28, 2026

(54) ULTRASOUND DIAGNOSTIC APPARATUS FOR DETERMINING SITUATION OF EXAMINATION

(71) Applicant: FUJIFILM Healthcare Corporation, Chiba (JP)

(72) Inventors: Teiichiro Ikeda, Tokyo (JP); Nobuhiko Fujii, Chiba (JP); Takehiro Tsujita, Chiba (JP); Natsumi Danno, Chiba (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 18/766,619

(22) Filed: Jul. 8, 2024

(65) Prior Publication Data

US 2025/0057509 A1     Feb. 20, 2025

(30) Foreign Application Priority Data

Aug. 14, 2023     (JP) ................................. 2023-132114

(51) Int. Cl.
*A61B 8/00*          (2006.01)
(52) U.S. Cl.
CPC ............ *A61B 8/5207* (2013.01); *A61B 8/461* (2013.01)
(58) Field of Classification Search
None
See application file for complete search history.

(56) References Cited

U.S. PATENT DOCUMENTS

| 2014/0206999 A1* | 7/2014 | Ohta | A61B 8/467 |
| | | | 600/447 |
| 2016/0000409 A1* | 1/2016 | Bruder | A61B 8/0833 |
| | | | 600/437 |
| 2020/0286214 A1* | 9/2020 | Kaneko | G06T 11/003 |
| 2022/0414837 A1* | 12/2022 | Kaneko | G16H 30/20 |
| 2023/0196580 A1* | 6/2023 | Inoue | G06T 7/74 |
| | | | 382/128 |
| 2023/0368917 A1* | 11/2023 | Kasahara | G16H 50/20 |

FOREIGN PATENT DOCUMENTS

| JP | H04224738 | 8/1992 |
| JP | 2007167116 | 7/2007 |
| JP | 2010029351 | 2/2010 |

* cited by examiner

*Primary Examiner* — Nyrobi Celestine
(74) *Attorney, Agent, or Firm* — JCIPRNET

(57)          ABSTRACT

A diagnostic site determination unit receives a plurality of ultrasound images successively acquired through transmission and reception of ultrasonic waves and determines a diagnostic site represented by each of the plurality of ultrasound images. An examination situation determination unit determines a situation of an examination using the ultrasonic waves based on a temporal change in a degree of certainty of the determination of the diagnostic site.

7 Claims, 4 Drawing Sheets

FIG. 2

ULTRASOUND DIAGNOSTIC APPARATUS FOR DETERMINING SITUATION OF EXAMINATION

CROSS-REFERENCE TO RELATED APPLICATION

This application claims the priority benefits of Japanese application no. 2023-132114, filed on Aug. 14, 2023. The entirety of the above-mentioned patent application is hereby incorporated by reference herein and made a part of this specification.

BACKGROUND

1. Technical Field

The present disclosure relates to an ultrasound diagnostic apparatus and a program.

2. Description of the Related Art

In an ultrasonic examination, an imaging mode or an image quality parameter corresponding to a situation of the examination may be selected to perform imaging. For example, a situation in which a rough scan is performed, a situation in which a scan for searching for a specific cross section is performed, a measurement situation, a situation in which an image is stored, and the like are examples of the situation of the examination. In general, the imaging mode or the image quality parameter corresponding to the situation of the examination is selected (for example, the image quality parameter is changed for each situation), and imaging is performed in accordance with a condition according to the situation of the examination.

JP1992-224738A (JP-H4-224738A) discloses a device that searches for pattern data similar to an image pattern and that outputs a diagnostic site corresponding to the pattern data.

JP2007-167116A discloses a device that reads out an image parameter associated with searched for patient information and that uses the image parameter as an image parameter corresponding to a diagnostic target site.

JP2010-029351A discloses a device that acquires diagnostic information regarding a subject and that adjusts an image parameter based on the diagnostic information.

SUMMARY

It is considered that a user such as a doctor or an examination technician manually selects the imaging mode or the image quality parameter corresponding to the situation of the examination. However, it is not easy for the user himself/herself to accurately grasp the situation of the examination. Therefore, it is not easy for the user to manually select the imaging mode or the image quality parameter corresponding to the situation of the examination. In addition, since experience is required in order to select the imaging mode or the image quality parameter corresponding to the situation of the examination, the selection may take time. Even for a skilled person, it is not easy to manually select the imaging mode or the image quality parameter corresponding to the situation of the examination. As a result, a time required for the entire examination may be lengthened. Therefore, it is important to determine the situation of the examination.

An object of the present disclosure is to determine a situation of an examination from a plurality of ultrasound images successively acquired.

According to one aspect of the present disclosure, there is provided an ultrasound diagnostic apparatus comprising: an acquisition unit that successively acquires a plurality of ultrasound images through transmission and reception of ultrasonic waves; a diagnostic site determination unit that determines a diagnostic site represented by each of the plurality of ultrasound images; and an examination situation determination unit that determines a situation of an examination using the ultrasonic waves based on a temporal change in a degree of certainty of the determination of the diagnostic site.

The examination situation determination unit may determine the situation of the examination based on at least one of a magnitude of the degree of certainty or a variation in the degree of certainty.

The examination situation determination unit may determine the situation of the examination by changing a determination criterion using at least one of the magnitude of the degree of certainty or the variation in the degree of certainty according to an attribute of a user of the ultrasound diagnostic apparatus.

The acquisition unit may acquire the ultrasound image by transmitting and receiving the ultrasonic waves in accordance with an imaging mode corresponding to the situation of the examination determined by the examination situation determination unit.

The acquisition unit may adjust an image quality of the ultrasound image in accordance with an image quality parameter corresponding to the situation of the examination determined by the examination situation determination unit.

The examination situation determination unit may further determine an image quality of the ultrasound image acquired by the acquisition unit and output information regarding the image quality.

The ultrasound diagnostic apparatus may further comprise: a presentation unit that presents processing to be subsequently performed to a user according to a determination result of the image quality of the ultrasound image acquired by the acquisition unit.

The ultrasound diagnostic apparatus may further comprise: a display controller that displays, on a display, a specific region represented in the ultrasound image acquired by the acquisition unit in accordance with a display aspect corresponding to the situation of the examination determined by the examination situation determination unit.

According to another aspect of the present disclosure, there is provided a program for causing a computer to function as: a diagnostic site determination unit that receives a plurality of ultrasound images successively acquired through transmission and reception of ultrasonic waves and that determines a diagnostic site represented by each of the plurality of ultrasound images; and an examination situation determination unit that determines a situation of an examination using the ultrasonic waves based on a temporal change in a degree of certainty of the determination of the diagnostic site.

According to the present disclosure, it is possible to determine a situation of an examination from a plurality of ultrasound images successively acquired.

BRIEF DESCRIPTION OF THE DRAWINGS

FIG. 2 is a diagram showing an examination sequence.

DESCRIPTION OF THE EMBODIMENTS

Figure 1:
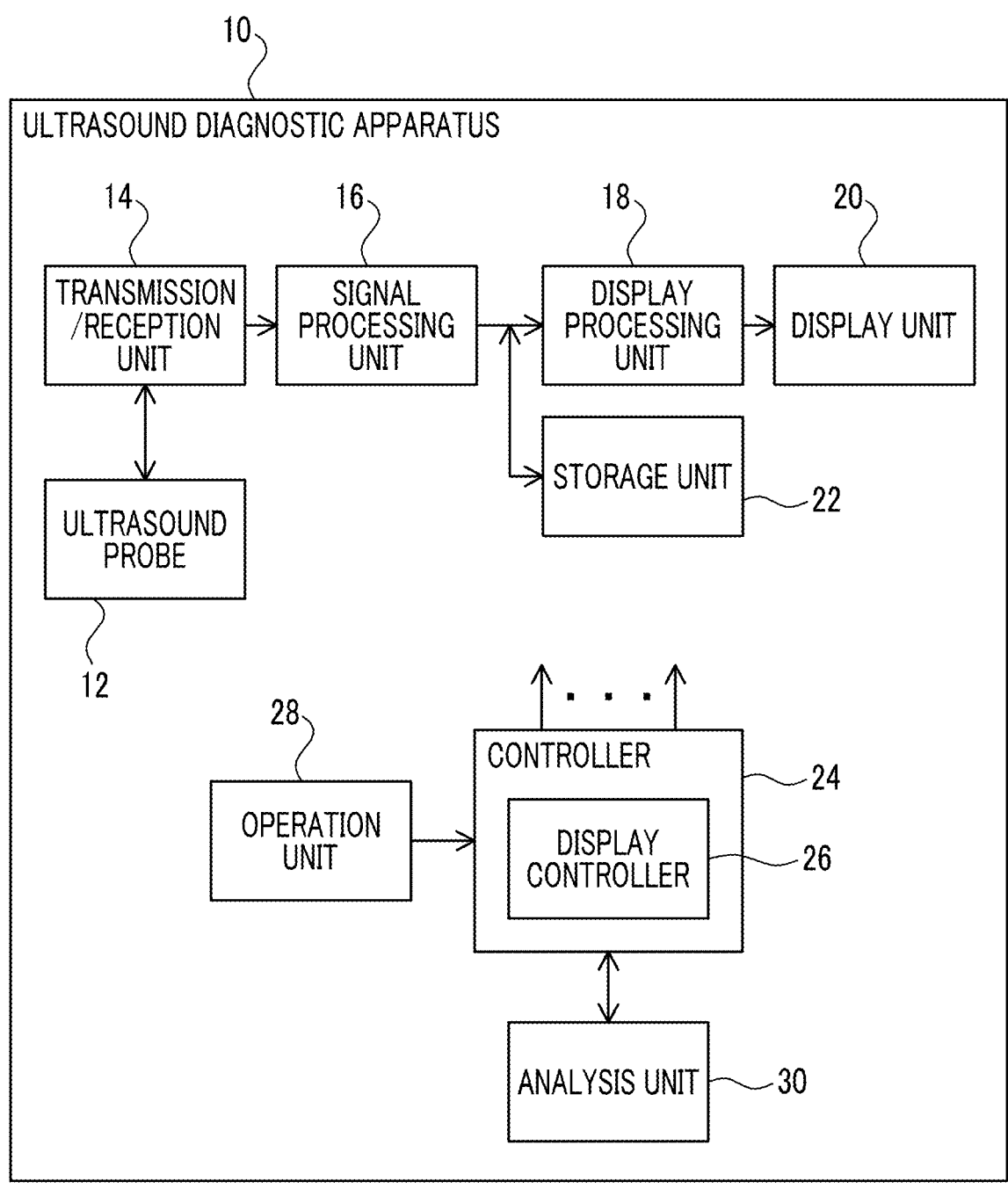
FIG. 1 is a block diagram showing an example of a configuration of an ultrasound diagnostic apparatus according to an embodiment.

An ultrasound diagnostic apparatus 10 according to an embodiment will be described with reference to FIG. 1. FIG. 1 is a block diagram showing an example of a configuration of the ultrasound diagnostic apparatus 10 according to the embodiment.

The ultrasound diagnostic apparatus 10 generates an ultrasound image representing an internal tissue of a subject by transmitting ultrasonic waves into the subject through an ultrasound probe 12 and receiving the ultrasonic waves reflected in the subject.

The ultrasound probe 12 is a device that transmits and receives the ultrasonic waves. For example, the ultrasound probe 12 includes a 1D array oscillator. The 1D array oscillator includes a plurality of ultrasound oscillators arranged in one dimension. An ultrasonic beam is formed by the 1D array oscillator, and electron scanning with the ultrasonic beam is repeatedly performed. As a result, a scanning plane is formed in a living body for each electron scanning. The ultrasound probe 12 may include, instead of the 1D array oscillator, a 2D array oscillator formed to include a plurality of ultrasound oscillators arranged in two dimensions. As a scanning method, sector scanning, linear scanning, convex scanning, or the like is used.

A transmission/reception unit 14 functions as a transmission beam former and a reception beam former. In the transmission, the transmission/reception unit 14 supplies a plurality of transmission signals having a certain delay relationship to the plurality of ultrasound oscillators included in the ultrasound probe 12. As a result, a transmission beam of the ultrasonic wave is formed. In the reception, a reflected wave (RF signal) from the living body is received by the ultrasound probe 12. As a result, a plurality of reception signals are output from the ultrasound probe 12 to the transmission/reception unit 14. The transmission/reception unit 14 forms a reception beam by applying phasing addition processing to the plurality of reception signals. Data of the reception beam is output to a signal processing unit 16. That is, the transmission/reception unit 14 forms the reception beam by performing delay processing on the reception signal obtained from each ultrasound oscillator in accordance with a delay processing condition for each ultrasound oscillator and performing addition processing on the plurality of reception signals obtained from the plurality of ultrasound oscillators. The delay processing condition is defined by reception delay data indicating a delay time. A reception delay data set (that is, a set of delay times) corresponding to the plurality of ultrasound oscillators is supplied from a controller 24.

The signal processing unit 16 generates an ultrasound image (for example, a B-mode image) by applying, to the beam data output from the transmission/reception unit 14, signal processing such as detection, amplitude compression (amplitude transform) such as logarithmic compression, and a conversion function (a coordinate transformation function and an interpolation processing function by a digital scan converter (DSC)). The ultrasound image is not limited to the B-mode image, and may be a color Doppler image, a pulse Doppler image, a strain image, a shear wave elastography image, or the like.

The transmission/reception unit 14 and the signal processing unit 16 correspond to an example of an acquisition unit.

A display processing unit 18 generates a display image by overlaying necessary graphic data on the ultrasound image. The display image is output to a display unit 20. One or a plurality of images are arranged and displayed in a display aspect according to a display mode.

The display unit 20 is a display such as a liquid crystal display or an EL display. The ultrasound image such as the B-mode image is displayed on the display unit 20. The display unit 20 may be a device comprising both the display and an operation unit 28. For example, a graphic user interface (GUI) may be realized by the display unit 20. In addition, a user interface such as a touch panel may be realized by the display unit 20.

A storage unit 22 constitutes one or a plurality of storage regions for storing data. The storage unit 22 is, for example, a hard disk drive (HDD), a solid state drive (SSD), various memories (for example, RAM, DRAM, or ROM), other storage devices (for example, optical disk), or a combination thereof. The image generated through the imaging of the ultrasound diagnostic apparatus 10, information indicating an imaging condition, information regarding a patient, and the like are stored in the storage unit 22.

The controller 24 controls an operation of each unit of the ultrasound diagnostic apparatus 10. The controller 24 includes a display controller 26.

The display controller 26 displays the ultrasound image on the display unit 20. The display controller 26 may display information or an image other than the ultrasound image on the display unit 20.

The operation unit 28 is a device for a user to input a condition, a command, and the like necessary for imaging, to the ultrasound diagnostic apparatus 10. For example, the operation unit 28 is an operation panel, a switch, a button, a keyboard, a mouse, a track ball, or a joystick.

An analysis unit 30 analyzes the ultrasound image to determine a situation of an examination using the ultrasonic waves.

For example, the examination using the ultrasonic waves includes a plurality of processes. Each process is executed in accordance with a predetermined procedure. The situation of the examination using the ultrasonic waves is a process or stage of the examination using the ultrasonic waves. Determining the situation of the examination using the ultrasonic waves is to specify a process or stage of the examination using the ultrasonic waves.

For example, a procedure of each process is predetermined as an examination protocol. Information indicating the examination protocol (that is, information indicating the procedure of each process) is previously stored in the storage unit 22. The examination protocol is previously created according to an examination purpose, an examination site, a medical department, or the like, and is configured of a combination of one or more processes. The ultrasound diagnostic apparatus 10 operates in accordance with the examination protocol, thereby supporting work (for example, examination work or diagnostic work) of the user such as a doctor or an examination technician. The ultrasound diagnostic apparatus 10 has a protocol assistant function as an examination support function.

For example, the examination protocol is determined for each examination site or for each medical department. Information indicating the examination protocol for each examination site or information indicating the examination protocol for each medical department is previously stored in the storage unit 22. The examination site is an abdomen, a chest, a heart, a blood vessel, a neck, a urinary organ, or the like. The medical department is an internal medicine department, a surgery department, an obstetrics and gynecology department, a radiology department, or the like. Of course, the examination site and the medical department are not limited to these. Examples of the situation of the examination include a situation in which the ultrasound image is acquired, a situation in which a scan for searching for a specific cross section to be scanned with the ultrasonic waves is performed, a situation in which measurement is performed using the ultrasound image, and a situation in which the ultrasound image is stored. That is, examples of the process of the examination include a process of acquiring the ultrasound image, a process of performing a scan for searching for a specific cross section to be scanned with the ultrasonic waves, a process of performing measurement using the ultrasound image, and a process of storing the ultrasound image.

For example, the process of acquiring the ultrasound image is a process of performing a rough scan. The rough scan is a scan with a lower density of scanning lines (for example, a density of the transmission beam in a scanning plane) than a more detailed scan.

For example, in the process of performing the scan for searching for the specific cross section, the rough scan or the detailed scan is executed.

A result of the analysis by the analysis unit 30 may be used for the acquisition of the ultrasound image (that is, the transmission and reception of the ultrasonic waves). For example, imaging or the like may be performed according to the result of the analysis by the analysis unit 30.

Figure 2:
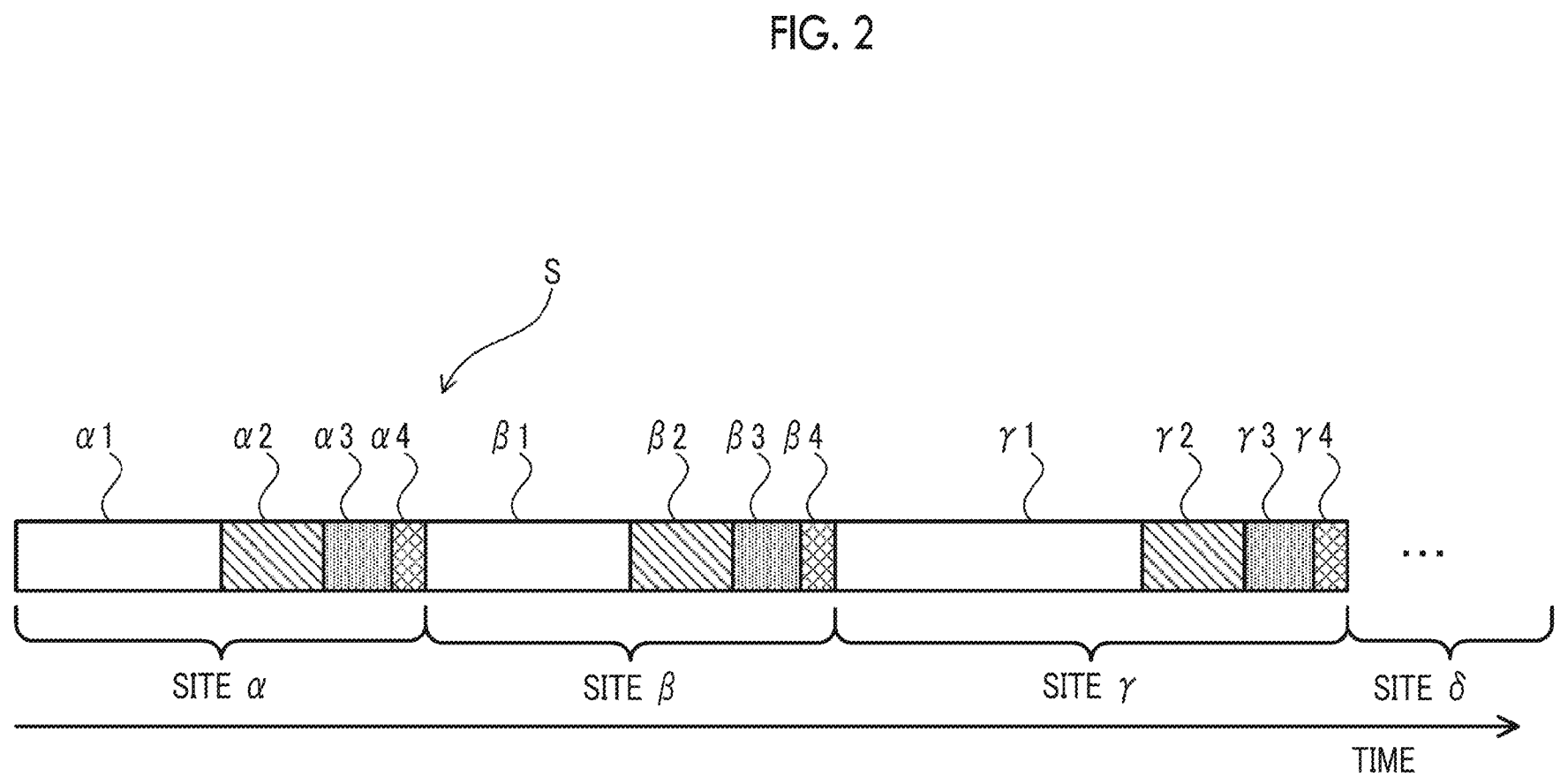

An examination sequence will be described with reference to FIG. 2. FIG. 2 shows an example of the examination sequence. A horizontal axis represents time.

An examination sequence S includes an examination for each of sites α, β, γ, δ, and the like. For example, the examination for each site is executed in accordance with the examination protocol. That is, the user operates the ultrasound diagnostic apparatus 10 in accordance with the examination protocol, thereby executing each process included in the examination protocol. Of course, the examination for each site may be executed without following the examination protocol. For example, the user may operate the ultrasound diagnostic apparatus 10 without following the examination protocol, thereby executing processing (for example, acquisition or measurement of the ultrasound image) that is not included in the examination protocol.

For example, the examination for the site α includes processes α1, α2, α3, and α4.

The process α1 is a process of performing a rough scan. For example, in the process α1, a scan with a low density of scanning lines is executed. As a result, an ultrasound image having a lower image quality than the ultrasound image generated by executing the more detailed scan is generated. For example, in a case where the user operates the operation unit 28 to issue an instruction to execute the rough scan, the transmission/reception unit 14 executes the rough scan under the control of the controller 24. For example, the ultrasound image generated by executing the rough scan is displayed on the display unit 20. The user determines whether or not the site α is represented in the ultrasound image by referring to the ultrasound image.

The process α2 is a process of searching for the specific cross section to be scanned with the ultrasonic waves. For example, in the process α2, the rough scan or the detailed scan is executed to generate the ultrasound image. The ultrasound image is displayed on the display unit 20. The user determines whether or not a site in a specific cross section suitable for the diagnosis of the site α is represented in the ultrasound image by referring to the ultrasound image. For example, in the process α2, the user changes a position or an angle of the ultrasound probe 12 on a body surface of the subject such that an ultrasound image of a specific cross section suitable for the diagnosis of the site α is acquired. The user determines whether or not a site in a specific cross section is represented in the ultrasound image by referring to the ultrasound image while changing the position or the angle of the ultrasound probe 12.

The process α3 is a process of performing measurement. For example, in the process α3, the ultrasound image is generated by executing the detailed scan, and the measurement is executed using the ultrasound image as a target. The ultrasound diagnostic apparatus 10 has a plurality of different measurement functions. For example, the user operates the operation unit 28 to select Za measurement function from the plurality of different measurement functions and issues an instruction to execute the selected measurement function. The controller 24 executes the measurement on the ultrasound image by executing the designated measurement function. For example, a function of measuring a length or a size of the site is executed. Of course, a function different from this may be executed. For example, in a case where an ultrasound image representing a site in a specific cross section is acquired in the process α2, the process α3 is executed following the process α2.

The process α4 is a process of storing the ultrasound image. For example, in the process α4, the transmission and reception of the ultrasonic waves are performed without changing the position or the angle of the ultrasound probe 12 by the user. The user refers to the acquired ultrasound image displayed on the display unit 20 and operates the operation unit 28 to select an ultrasound image to be stored. The ultrasound image selected by the user is stored in the storage unit 22 or an external storage device. Information indicating the measurement result may be stored in the storage unit 22 by being linked with the ultrasound image.

The processes α1, α2, α3, and α4 are executed in this order, whereby the ultrasound image is generated in each process. The analysis unit 30 analyzes the generated ultrasound image to specify a process in which the ultrasound image is acquired (that is, the situation of the examination).

In the example shown in FIG. 2, the examination of the site α is executed after the examination of the site α is completed. The examination of the site β includes processes β1, β2, β3, and β4. In the examination of the site β as well, each process is executed in the same manner as in the examination of the site α. After the examination of the site β is completed, the examination for the site γ is executed. Thereafter, the examination or the like for the site δ is executed.

Figure 3:
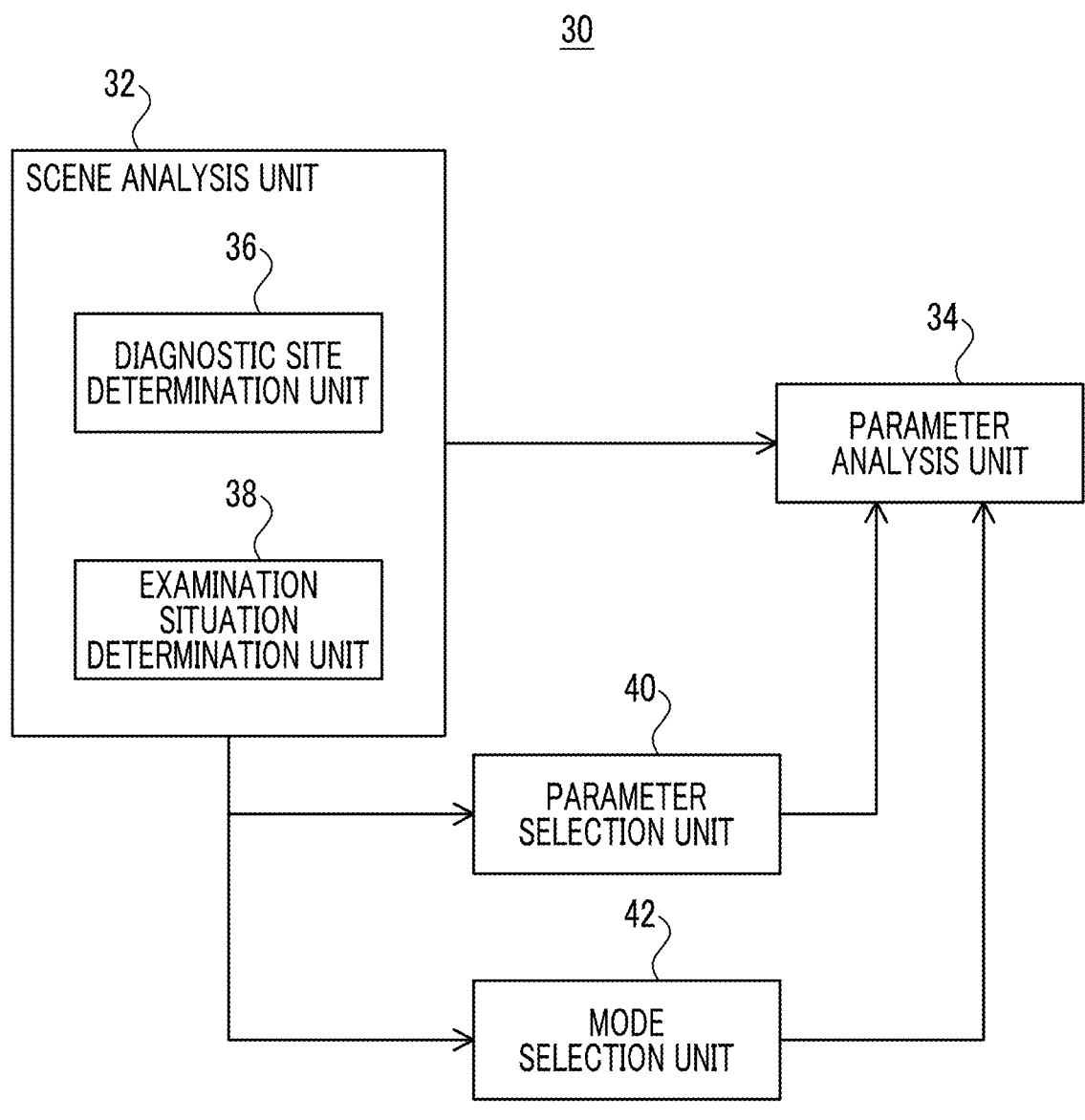
FIG. 3 is a block diagram showing an example of a configuration of an analysis unit.

A configuration of the analysis unit 30 will be described with reference to FIG. 3. FIG. 3 is a block diagram showing the configuration of the analysis unit 30.

The analysis unit 30 includes a scene analysis unit 32 and a parameter analysis unit 34. The scene analysis unit 32 analyzes the ultrasound image to determine the diagnostic site represented in the ultrasound image and to determine the situation of the examination. The parameter analysis unit 34 specifies an image quality parameter based on a result of the scene analysis unit 32, and outputs the specified result. For example, the transmission and reception of the ultrasonic waves are controlled or the image quality of the acquired ultrasound image is adjusted based on the output of the parameter analysis unit 34.

The scene analysis unit 32 includes a diagnostic site determination unit 36 and an examination situation determination unit 38.

The diagnostic site determination unit 36 determines the diagnostic site represented by the ultrasound image. For example, artificial intelligence (AI) is used for the determination. For example, machine learning is performed using an image representing the diagnostic site for each diagnostic site, so that the diagnostic site represented in the ultrasound image is determined, and a discriminator that discriminates the diagnostic site is generated. The diagnostic site determination unit 36 determines the diagnostic site represented in the ultrasound image by using the discriminator.

In addition, the diagnostic site determination unit 36 calculates a degree of certainty of the determination. The degree of certainty of the determination of the diagnostic site is a probability representing a certainty of the determination result. Specifically, the degree of certainty of the determination of the diagnostic site is a probability representing a certainty that the diagnostic site represented in the ultrasound image is the determined diagnostic site. That is, the degree of certainty of the determination of the diagnostic site is a probability that the diagnostic site represented in the ultrasound image is the determined diagnostic site.

The type of the artificial intelligence or machine learning used is not limited, and any algorithm or model may be used. For example, a convolutional neural network (CNN), a recurrent neural network (RNN), generative adversarial networks (GAN), linear models, random forests, decision tree learning, a support vector machine (SVM), an ensemble classifier, or other algorithms are used. In addition, pattern matching such as template matching, or algorithms that do not require learning such as correlation coefficients and similarity calculations may be applied to the processing by the diagnostic site determination unit 36.

The diagnostic site determination unit 36 calculates the degree of certainty for each diagnostic site. For example, in a case where N types of diagnostic sites are determined, the diagnostic site determination unit 36 calculates the degree of certainty for each of the N types of diagnostic sites. For example, the diagnostic site determination unit 36 determines that the diagnostic site having the highest degree of certainty is the diagnostic site represented in the ultrasound image.

The diagnostic site determination unit 36 may determine which cross section of the diagnostic site the scanning plane represented in the ultrasound image corresponds to. In this case, the diagnostic site determination unit 36 calculates the degree of certainty of the determination (that is, a probability representing a certainty that the scanning plane is the determined cross section).

A plurality of ultrasound images are successively acquired by the transmission and reception of the ultrasonic waves. That is, a plurality of time-series ultrasound images are acquired. The diagnostic site determination unit 36 determines the diagnostic site represented by each of the plurality of ultrasound images. In addition, the diagnostic site determination unit 36 calculates the degree of certainty of the determination of each diagnostic site for each of the plurality of ultrasound images. As a result, a plurality of time-series degrees of certainty are calculated for each diagnostic site. That is, data representing a temporal change in the degree of certainty is generated for each diagnostic site.

The examination situation determination unit 38 determines the situation of the examination using the ultrasonic waves based on the temporal change in the degree of certainty of the determination of the diagnostic site. Specifically, the examination situation determination unit 38 specifies the process included in the examination using the ultrasonic waves based on the temporal change in the degree of certainty of the determination of the diagnostic site.

The examination situation determination unit 38 determines the situation of the examination based on at least one of a magnitude of the degree of certainty or a variation in the degree of certainty.

For example, the magnitude of the degree of certainty is an absolute value of the degree of certainty, an average value of the degree of certainty, a moving average value of the degree of certainty, or the like. For example, the examination situation determination unit 38 specifies the process included in the examination using the ultrasonic waves based on a temporal change in the absolute value of the degree of certainty, a temporal change in the average value of the degree of certainty, or a temporal change in the moving average value of the degree of certainty.

For example, the examination situation determination unit 38 specifies the process included in the examination using the ultrasonic waves based on a temporal change in the absolute value of the degree of certainty of the diagnostic site having the highest degree of certainty. The examination situation determination unit 38 may specify the process included in the examination using the ultrasonic waves based on a temporal change in the average value of the degree of certainty of the diagnostic site having the highest degree of certainty. The examination situation determination unit 38 may specify the process included in the examination using the ultrasonic waves based on a temporal change in the moving average value of the degree of certainty of the diagnostic site having the highest degree of certainty.

For example, the variation in the degree of certainty is a standard deviation, a variance, or a differential value of the degree of certainty. For example, the examination situation determination unit 38 specifies the process included in the examination using the ultrasonic waves based on a temporal change in the standard deviation of the degree of certainty, a temporal change in the variance of the degree of certainty, or a temporal change in the differential value of the degree of certainty.

Further, the analysis unit 30 includes a parameter selection unit 40 and a mode selection unit 42.

The parameter selection unit 40 selects the image quality parameter corresponding to the situation of the examination determined by the examination situation determination unit 38. That is, the parameter selection unit 40 selects the image quality parameter corresponding to the process specified by the examination situation determination unit 38. For example, for each process of the examination, the information indicating the process and the image quality parameter for acquiring or displaying the ultrasound image suitable for the process are previously linked to each other. Information indicating the linkage is previously stored in the storage unit 22.

For example, the image quality parameter is a sound velocity of the ultrasonic waves transmitted from the ultrasound probe 12, a gain of the ultrasound image, a contrast of the ultrasound image, a frequency of the ultrasonic waves transmitted from the ultrasound probe 12, power of the ultrasonic waves transmitted from the ultrasound probe 12, a depth of the display of the ultrasound image, a cutoff frequency of a filter, a notch frequency, and the like.

For example, the image quality parameter selected by the parameter selection unit 40 is output to the controller 24. The controller 24 controls the transmission and reception of the ultrasonic waves by the transmission/reception unit 14 or adjusts the image quality of the ultrasound image acquired by the transmission and reception of the ultrasonic waves in accordance with the selected image quality parameter. The image quality parameter selected by the parameter selection unit 40 may be output to the parameter analysis unit 34.

With reference to the example shown in FIG. 2, the image quality parameter suitable for the process α1, the image quality parameter suitable for the process α2, the image quality parameter suitable for the process α3, and the image quality parameter suitable for the process α4 are predetermined. These image quality parameters are previously stored in the storage unit 22.

For example, in a case where the examination situation determination unit 38 determines that the process of the examination is the process α1, the parameter selection unit 40 selects the image quality parameter linked to the process α1. For example, the transmission and reception of the ultrasonic waves by the transmission/reception unit 14 are controlled or the image quality of the ultrasound image acquired by the transmission and reception of the ultrasonic waves is adjusted in accordance with the selected image quality parameter. The selected image quality parameter may be output to the parameter analysis unit 34.

The mode selection unit 42 selects the imaging mode corresponding to the situation of the examination determined by the examination situation determination unit 38. That is, the mode selection unit 42 selects the imaging mode corresponding to the process specified by the examination situation determination unit 38. For example, for each process of the examination, the information indicating the process and the information indicating the imaging mode for acquiring or displaying the ultrasound image suitable for the process are previously linked to each other. Information indicating the linkage is previously stored in the storage unit 22.

For example, the imaging mode includes a harmonic imaging method, focus adjustment of the ultrasonic waves transmitted from the ultrasound probe 12, a coherent factor, frequency compound processing (for example, processing of combining an ultrasound image acquired by transmitting and receiving high-frequency ultrasonic waves and an ultrasound image acquired by transmitting and receiving low-frequency ultrasonic waves), and spatial compound processing.

For example, the information indicating the imaging mode selected by the mode selection unit 42 is output to the controller 24. The controller 24 controls the transmission and reception of the ultrasonic waves by the transmission/reception unit 14 in accordance with the selected imaging mode. The information indicating the imaging mode selected by the mode selection unit 42 may be output to the parameter analysis unit 34.

With reference to the example shown in FIG. 2, the imaging mode suitable for the process α1, the imaging mode suitable for the process α2, the imaging mode suitable for the process α3, and the imaging mode suitable for the process α4 are predetermined. Information indicating these imaging modes is previously stored in the storage unit 22.

For example, in a case where the examination situation determination unit 38 determines that the process of the examination is the process α1, the mode selection unit 42 selects the imaging mode linked to the process α1. For example, the transmission and reception of the ultrasonic waves by the transmission/reception unit 14 are controlled in accordance with the selected imaging mode. Information indicating the selected imaging mode may be output to the parameter analysis unit 34.

The parameter analysis unit 34 selects the image quality parameter suitable for the imaging mode based on the image quality parameter selected by the parameter selection unit 40 and on the imaging mode selected by the mode selection unit 42. For example, the image quality parameter suitable for the imaging mode is predetermined for each imaging mode, and the parameter analysis unit 34 selects the image quality parameter corresponding to the selected imaging mode. The selected image quality parameter is output to the controller 24. The controller 24 controls the transmission and reception of the ultrasonic waves by the transmission/reception unit 14 or adjusts the image quality of the ultrasound image acquired by the transmission and reception of the ultrasonic waves in accordance with the selected image quality parameter.

Figure 4:
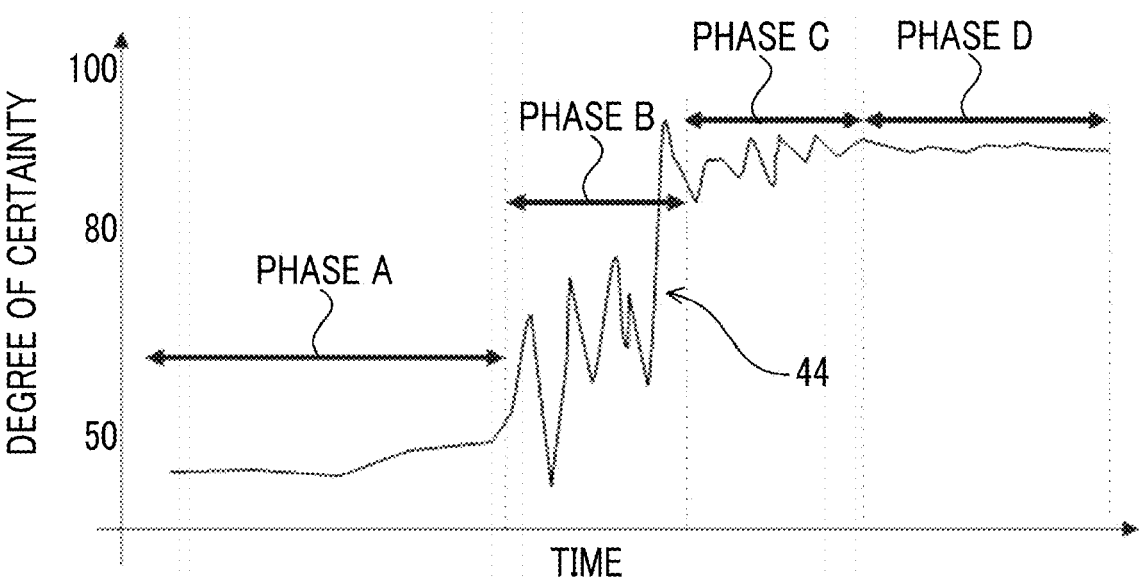
FIG. 4 is a diagram showing a temporal change in a degree of certainty.

Hereinafter, a specific example of the processing by the scene analysis unit 32 will be described with reference to FIG. 4. FIG. 4 shows a temporal change in the degree of certainty.

A horizontal axis in FIG. 4 represents time. A vertical axis represents the degree of certainty calculated by the diagnostic site determination unit 36. For example, the degree of certainty of the diagnostic site having the highest degree of certainty among the plurality of diagnostic sites is the degree of certainty shown on the vertical axis. A graph 44 shown in FIG. 4 represents a temporal change in the degree of certainty.

For example, in a case where the diagnostic site determination unit 36 determines that the diagnostic site having the highest degree of certainty is continuously changed, the examination situation determination unit 38 determines that the situation of the examination is a screening phase. The screening phase is the process (for example, the process α1) in which the rough scan is executed. Phase A shown in FIG. 4 is an example of the screening phase. For example, in a case where a situation in which the highest degree of certainty is equal to or lower than a first threshold value continues for a predetermined time or longer, the examination situation determination unit 38 determines that the situation of the examination is the screening phase. The first threshold value is a predetermined value. The first threshold value may be changed by the user.

For example, in a case where a plurality of ultrasound images representing the same diagnostic site are acquired and the diagnostic site determination unit 36 determines that the plurality of ultrasound images represent different cross sections, the examination situation determination unit 38 determines that the situation of the examination is a cross-section identification phase. The cross-section identification phase is the process (for example, the process α2) of searching for the specific cross section to be scanned with the ultrasonic waves. The cross-section identification phase can also be said to be a semi-diagnosis mode. For example, in a case where the ultrasound images representing the different cross sections of the same diagnostic site are discretely acquired, the examination situation determination unit 38 determines that the situation of the examination is the cross-section identification phase. Phase B shown in FIG. 4 is an example of the cross-section identification phase. For example, in a case where a differential (that is, an inclination) of a moving average with the highest degree of certainty is equal to or higher than a second threshold value, the examination situation determination unit 38 determines that the situation of the examination is the cross-section identification phase. As another example, in a case where a variance value of the highest degree of certainty is equal to or higher than a third threshold value, the examination situation determination unit 38 may determine that the situation of the examination is the cross-section identification phase. Further, as still another example, in a case where a variation value (for example, a difference in the degree of certainty) per unit time of the highest degree of certainty is equal to or higher than a fourth threshold value, the examination situation determination unit 38 may determine that the situation of the examination is the cross-section identification phase. The second threshold value, the third threshold value, and the fourth threshold value are predetermined values. The second threshold value, the third threshold value, and the fourth threshold value may be changed by the user.

For example, in a case where the diagnostic site determination unit 36 determines that the ultrasound images representing the same cross section of the same diagnostic site are continuously acquired, the examination situation determination unit 38 determines that the situation of the examination is a diagnose phase. The diagnose phase is a process in which the user performs diagnosis by referring to the ultrasound image. The measurement (for example, the process α3) may be performed in the diagnose phase. Phase C shown in FIG. 4 is an example of the diagnose phase. For example, in a case where the highest degree of certainty is equal to or higher than a fifth threshold value and the differential of the moving average with the highest degree of certainty is lower than the second threshold value and is equal to or higher than a sixth threshold value, the examination situation determination unit 38 determines that the situation of the examination is the diagnose phase. As another example, in a case where the highest degree of certainty is equal to or higher than the fifth threshold value and the variance value of the highest degree of certainty is lower than the third threshold value and is equal to or higher than a seventh threshold value, the examination situation determination unit 38 may determine that the situation of the examination is the diagnose phase. Further, as still another example, in a case where the highest degree of certainty is equal to or higher than the fifth threshold value and the variation value per unit time of the degree of certainty is lower than the fourth threshold value and is equal to or higher than an eighth threshold value, the examination situation determination unit 38 may determine that the situation of the examination is the diagnose phase. The sixth threshold value is a value smaller than the second threshold value. The seventh threshold value is a value smaller than the third threshold value. The eighth threshold value is a value smaller than the fourth threshold value. The fifth threshold value, the sixth threshold value, the seventh threshold value, and the eighth threshold value are predetermined values. The fifth threshold value, the sixth threshold value, the seventh threshold value, and the eighth threshold value may be changed by the user.

For example, in a case where the ultrasound images representing the same cross section of the same diagnostic site are continuously acquired and the diagnostic site determination unit 36 determines that the highest degree of certainty is almost unchanged, the examination situation determination unit 38 determines that the situation of the examination is a reporting phase. The reporting phase is the process (for example, the process α4) of capturing an ultrasound image for storage for creating a report. Phase D shown in FIG. 4 is an example of the reporting phase. For example, in a case where the highest degree of certainty is equal to or higher than the fifth threshold value and the differential of the moving average with the highest degree of certainty is lower than the sixth threshold value, the examination situation determination unit 38 determines that the situation of the examination is the reporting phase. As another example, in a case where the highest degree of certainty is equal to or higher than the fifth threshold value and the variance value of the highest degree of certainty is lower than the seventh threshold value, the examination situation determination unit 38 may determine that the situation of the examination is the reporting phase. Further, as still another example, in a case where the highest degree of certainty is equal to or higher than the fifth threshold value and the variation value per unit time of the degree of certainty is lower than the eighth threshold value, the examination situation determination unit 38 may determine that the situation of the examination is the reporting phase. That is, in a case where the variation in the degree of certainty is smaller than the variation in the degree of certainty in the diagnose phase, the examination situation determination unit 38 determines that the situation of examination is the reporting phase.

The display controller 26 may display the result of the scene analysis unit 32 on the display unit 20. For example, in a case where the current examination situation is the process α1, the display controller 26 displays information indicating that the current examination situation is the process α1 on the display unit 20. As a result, the user can check the current examination situation.

The examination situation determination unit 38 may determine the situation of the examination by changing a determination criterion using at least one of the magnitude of the degree of certainty or the variation in the degree of certainty according to an attribute of the user of the ultrasound diagnostic apparatus 10.

For example, the attribute of the user is a skill level for imaging or examination using the ultrasonic waves, or a qualification of the user. For example, the skill level is the number of years of experience in imaging or examination using the ultrasonic waves. The higher the number of years of experience is, the higher the skill level is. For example, the qualification is a doctor, a nurse, a medical radiologist, or a clinical laboratory technician.

For example, in a case where imaging or examination is performed using the ultrasound diagnostic apparatus 10, attribute information indicating the attribute of the user is input to the ultrasound diagnostic apparatus 10. For example, the user inputs the attribute information of the user to the ultrasound diagnostic apparatus 10 by using the operation unit 28. The attribute information of the user is stored in an IC card, and the information stored in the IC card is read by the ultrasound diagnostic apparatus 10, so that the attribute information may be input to the ultrasound diagnostic apparatus 10. The examination situation determination unit 38 determines the situation of the examination by changing the determination criterion according to the attribute indicated by the input attribute information.

For example, the determination criterion is a threshold value for the degree of certainty, a threshold value for the variation (for example, the variance or the differential value) in the degree of certainty, or the like. For example, the determination criterion is a threshold value such as the first threshold value to the eighth threshold value described above. For example, the examination situation determination unit 38 determines the situation of the examination by changing the first threshold value to the eighth threshold value according to the attribute of the user.

For example, the examination situation determination unit 38 may set each threshold value to be higher or lower as the skill level is higher. For example, each threshold value according to the skill level is predetermined, and the examination situation determination unit 38 determines the situation of the examination by using each threshold value according to the skill level.

The examination situation determination unit 38 may set each threshold value to be high or low according to the qualification of the user. For example, each threshold value according to the qualification of the user is predetermined, and the examination situation determination unit 38 determines the situation of the examination by using each threshold value according to the qualification of the user.

The examination situation determination unit 38 may define a plurality of processes as one process and determine the situation of the examination according to the skill level of the user. In the example shown in FIG. 4, the examination situation determination unit 38 may define a plurality of time phases as one time phase and determine the situation of the examination according to the skill level of the user. For example, in a case where the skill level is equal to or higher than the threshold value, the examination situation determination unit 38 defines the screening phase and the cross-section identification phase as one time phase, and determines whether or not the situation of the examination is the one time phase by using a threshold value corresponding to the one time phase. In a case where the skill level is lower than the threshold value, the examination situation determination unit 38 determines the situation of the examination separately for the screening phase and the cross-section identification phase. That is, it is assumed that the user whose skill level is equal to or higher than the threshold value can determine the situation of the examination even in a case where the examination situation determination unit 38 does not determine the situation of the examination separately for the screening phase and the cross-section identification phase. On the other hand, the user whose skill level is equal to or lower than the threshold value may be unable to determine the situation of the examination unless the examination situation determination unit 38 determines the situation of the examination separately for the screening phase and the cross-section identification phase. Therefore, in a case where the skill level of the user is equal to or higher than the threshold value, it is possible to prevent the unnecessary processing of performing the determination separately for the screening phase and the cross-section identification phase. In a case where the skill level of the user is lower than the threshold value, the situation of the examination is determined separately for the screening phase and the cross-section identification phase, so that processing that is useful for the user is executed.

In a case where the situation of the examination is determined by the examination situation determination unit 38, the mode selection unit 42 may select the imaging mode corresponding to the situation of the examination. In this case, the controller 24 controls the transmission and reception of the ultrasonic waves by the transmission/reception unit 14 or adjusts the image quality of the ultrasound image acquired by the transmission and reception of the ultrasonic waves in accordance with the selected imaging mode.

In addition, the parameter selection unit 40 may select the image quality parameter corresponding to the determined situation of the examination. In this case, the controller 24 adjusts the image quality of the ultrasound image in accordance with the selected image quality parameter.

For example, in a case where it is determined that the current examination situation is the screening phase, the mode selection unit 42 selects the imaging mode corresponding to the screening phase, and the parameter selection unit 40 selects the image quality parameter corresponding to the screening phase. As a result, the transmission and reception of the ultrasonic waves are performed in accordance with the imaging mode corresponding to the screening phase, and the ultrasound image is adjusted in accordance with the image quality parameter corresponding to the screening phase. As a result, an ultrasound image suitable for the screening phase is displayed. The user can perform an observation, an examination, or the like to be performed in the screening phase by referring to the ultrasound image.

In a time phase other than the screening phase, the imaging mode and the image quality parameter corresponding to the time phase are selected in the same manner as in the screening phase. The transmission and reception of the ultrasonic waves according to the imaging mode, the adjustment of the ultrasound image according to the image quality parameter, and the like are performed. As a result, the user can perform an observation, an examination, or the like suitable for the time phase.

Since the imaging mode and the image quality parameter are automatically set, it is possible to reduce a burden on the user to adjust the imaging mode and the image quality parameter. In addition, the efficiency of the ultrasonic examination is improved, and as a result, a burden on the patient can be reduced.

Hereinafter, other embodiments will be described.

The examination situation determination unit 38 may determine the image quality of the ultrasound image acquired by the transmission and reception of the ultrasonic waves, and may output information regarding the image quality. For example, the display controller 26 displays the information regarding the image quality on the display unit 20. The display controller 26 may display the information indicating the situation of the examination and the information regarding the image quality on the display unit 20.

For example, the image quality of the ultrasound image is a distribution of a contrast and a distribution of a brightness of the ultrasound image, the presence or absence of a defective portion (for example, a low brightness region of an end portion caused by floating of the ultrasound probe 12 from a body surface or the like) in the ultrasound image, the presence or absence of a shake or a blur of the ultrasound image caused by the operation of the ultrasound probe 12 by the user or a body movement, and the like. For example, the shake or the blur of the ultrasound image is determined as a decrease in speckle resolution. For example, the display controller 26 displays the information on the display unit 20 as information regarding the image quality.

By displaying the information indicating the situation of the examination and the information regarding the image quality, the user can check the image quality of the ultrasound image acquired in the situation, in addition to the situation of the examination.

The controller 24 may present processing to be subsequently performed to the user according to the determination result of the image quality of the ultrasound image. For example, the display controller 26 displays information indicating the processing to be subsequently performed on the display unit 20. The controller 24 corresponds to an example of a presentation unit.

For example, the controller 24 determines whether or not to perform the image quality adjustment of the subsequent stage based on the determination result of the image quality of the ultrasound image. For example, a criterion indicating good image quality is predetermined. In a case where the examination situation determination unit 38 determines that the image quality of the ultrasound image satisfies the criterion and is good, the controller 24 does not perform the image quality adjustment. In this case, the display controller 26 displays the information indicating that there is no need to perform the image quality adjustment on the display unit 20. On the other hand, in a case where the examination situation determination unit 38 determines that the image quality of the ultrasound image does not satisfy the criterion and is not good, the display controller 26 displays information for prompting the user to perform the image quality adjustment on the display unit 20. For example, the display controller 26 displays information for prompting the user to improve the position, the pushing force, and the like of the ultrasound probe 12 on the display unit 20 as information indicating the processing to be subsequently performed.

In addition, the controller 24 may reflect the information indicating the image quality of the ultrasound image in the report. For example, in a case where the image quality of the ultrasound image is good, the controller 24 records the symbol "○" in the report. In a case where the image quality of the ultrasound image is not good, the controller 24 records the symbol "Δ" in the report.

The controller 24 may feed back the result of the image quality adjustment to the scene analysis unit 32. For example, the controller 24 feeds back a result of improving the image quality or a result of not improving the image quality to the scene analysis unit 32. The scene analysis unit 32 determines the image quality of the ultrasound image in response to the feedback. The result of the determination may be displayed on the display unit 20 or may be recorded in the report.

In a case where the examination situation determination unit 38 determines that the image quality of the ultrasound image is good, the controller 24 may automatically execute the subsequent examination mode (for example, Doppler imaging), or may display information prompting the user to execute the subsequent examination mode on the display unit 20.

The display controller 26 may display a specific region represented in the ultrasound image on the display unit 20 in accordance with the display mode corresponding to the situation of the examination determined by the examination situation determination unit 38.

For example, the examination situation determination unit 38 may determine the presence or absence or a position of a lesion on the scanning surface, or may determine the presence or absence or a position of a specific region of interest (ROI) determined for each diagnostic site. In a case where the lesion or the region of interest exists, the display controller 26 displays the ultrasound image representing the lesion or the region of interest on the display unit 20 and displays the lesion or the region of interest in an emphasized manner on the display unit 20. The display controller 26 may increase a resolution of the lesion or the region of interest and display the lesion or the region of interest on the display unit 20. The parameter selection unit 40 may select the image quality parameter for emphasizing the lesion or the region of interest, and the display controller 26 may display the ultrasound image on the display unit 20 in accordance with the image quality parameter. In this manner, it is possible to improve the ability to diagnose the lesion or the region of interest. As a technique of extracting the lesion or the region of interest, a known technique is used. For example, the lesion or the region of interest is extracted by matching processing or artificial intelligence.

In addition, an optimal image quality parameter specialized for each case or each imaging scene may be stored in the storage unit 22. For example, the image quality parameter selected by the parameter selection unit 40 is stored in the storage unit 22 as the optimal image quality parameter. The controller 24 adjusts the image quality of the ultrasound image using the stored optimal image quality parameter in subsequent examinations. For example, the optimal image quality parameter for each case or each imaging scene is stored in the storage unit 22. The controller 24 adjusts the image quality of the ultrasound image by using the optimal image quality parameter corresponding to the case or the imaging scene specified by the scene analysis unit 32. The optimal image quality parameter selected by the parameter selection unit 40 may be read out and used, or may be used as an initial value.

For example, the parameter selection unit 40 selects the image quality parameter applied to the ultrasound image having the highest degree of certainty as the optimal image quality parameter. In a case where the degree of certainty is low (for example, in a case where the degree of certainty is equal to or lower than the threshold value), the controller 24 may select the image quality parameter applied to the ultrasound image having the highest degree of certainty in the previous same imaging scene as the optimal image quality parameter.

Hereinafter, an application example of the present embodiment will be described.

For example, in a case where it is determined that the acquired ultrasound image is an image (for example, an image representing a liver) acquired in a state in which an end part of a transmission/reception surface of the ultrasound probe 12 is floated from the body surface of the subject, the parameter selection unit 40 selects the image quality parameter for gain adjustment. The controller 24 performs adjustment of suppressing the glare on the ultrasound image by using the selected image quality parameter. In a case where the floating of the ultrasound probe 12 is eliminated, a standard cross section is determined, and a liver segment is determined. The image quality and the imaging mode corresponding to the determined segment are selected, and the image quality of the ultrasound image is automatically adjusted. As a result, unnecessary image quality adjustment is prevented from being performed by the user, and necessary image quality adjustment is executed.

In addition, a scene (for example, a situation in which the transmission/reception surface of the ultrasound probe 12 is floating from the body surface of the subject, a situation in which a body movement of the subject is large, or a situation in which a diaphragm exists) is analyzed. As a result, it is possible to perform more detailed image quality adjustment than in the related art (automatic image quality adjustment based only on the analysis of the adjustment parameter). For example, in a case where the diaphragm is represented in the ultrasound image, processing of improving a contrast of a portion other than the diaphragm can be executed while avoiding clipping of a signal by reducing the gain of the diaphragm.

The signal processing unit 16, the display processing unit 18, the controller 24, the display controller 26, and the analysis unit 30 can be realized by using, for example, hardware resources such as a processor and an electronic circuit, and a device such as a memory may be used in the realization as necessary. In addition, the signal processing unit 16, the display processing unit 18, the controller 24, the display controller 26, and the analysis unit 30 may be realized by a computer, for example. That is, all or a part of the signal processing unit 16, the display processing unit 18, the controller 24, the display controller 26, and the analysis unit 30 may be realized by cooperation between hardware resources, such as a central processing unit (CPU) or a memory included in a computer, and software (program) that defines the operation of the CPU or the like. The program is stored in the storage unit 22 of the ultrasound diagnostic apparatus 10 or in another storage device through a recording medium, such as a CD or a DVD, or a communication path, such as a network. As another example, the signal processing unit 16, the display processing unit 18, the controller 24, the display controller 26, and the analysis unit 30 may be realized by a digital signal processor (DSP), an application specific integrated circuit (ASIC), a field programmable gate array (FPGA), or the like. Of course, a graphics processing unit (GPU) and the like may be used. The signal processing unit 16, the display processing unit 18, the controller 24, the display controller 26, and the analysis unit 30 may be realized by a single apparatus, or each of functions of the signal processing unit 16, the display processing unit 18, the controller 24, the display controller 26, and the analysis unit 30 may be realized by one or a plurality of apparatuses.

The function of the analysis unit 30 may be executed by an apparatus (for example, a personal computer or a server) other than the ultrasound diagnostic apparatus 10. In this case, the result of the analysis by the analysis unit 30 may be input to the ultrasound diagnostic apparatus 10.

What is claimed is:

1. An ultrasound diagnostic apparatus comprising:
a hardware processor configured to:
successively acquire a plurality of ultrasound images through transmission and reception of ultrasonic waves;
determine a diagnostic site represented by each of the plurality of ultrasound images; and
determine a situation of an examination using the ultrasonic waves based on a temporal change in a degree of certainty of the determination of the diagnostic site,
wherein the situation of the examination comprises at least one of a screening phase in which rough scan is executed to acquire the ultrasound image, a cross-section identification phase in which a scan for searching for a specific cross section to be scanned with the ultrasonic waves is performed, a diagnose phase in which measurement is performed using the ultrasound image, and a reporting phase in which the ultrasound image is stored for creating a report,
wherein the degree of certainty is a probability that the diagnostic site represented in the ultrasound image is a determined diagnostic site, and
wherein the hardware processor acquires one of the plurality of the ultrasound images by transmitting and receiving the ultrasonic waves in accordance with an imaging mode corresponding to the situation of the determined examination, wherein the imaging mode comprises one of a harmonic imaging method, a focus adjustment of the ultrasonic waves, a coherent factor, a frequency compound processing, and a spatial compound processing.

2. The ultrasound diagnostic apparatus according to claim 1,
wherein the hardware processor determines the situation of the examination based on at least one of a magnitude of the degree of certainty or a variation in the degree of certainty.

3. The ultrasound diagnostic apparatus according to claim 2,
wherein the hardware processor determines the situation of the examination by changing a determination criterion using at least one of the magnitude of the degree of certainty or the variation in the degree of certainty according to an attribute of a user of the ultrasound diagnostic apparatus, wherein the determination criterion is a threshold value for the degree of certainty, or a threshold value for a variation in the degree of certainty, and the attribute of the user is a skill level for imaging or examination using the ultrasonic waves, or a qualification of the user.

4. The ultrasound diagnostic apparatus according to claim 1,
wherein the hardware processor adjusts an image quality of one of the plurality of the ultrasound images in accordance with an image quality parameter corresponding to the situation of the determined examination, wherein the image quality parameter is a sound velocity of the ultrasonic waves, a gain of the ultrasound image, a contrast of the ultrasound image, a frequency of the ultrasonic waves, a power of the ultrasonic waves, a depth of display of the ultrasound image, a cutoff frequency of a filter, or a notch frequency.

5. The ultrasound diagnostic apparatus according to claim 1,
wherein the hardware processor further determines an image quality of one of the plurality of the ultrasound images and outputs the image quality.

6. The ultrasound diagnostic apparatus according to claim 5 wherein the hardware processor presents processing to be subsequently performed to a user according to the image quality of one of the plurality of the ultrasound images.

7. The ultrasound diagnostic apparatus according to claim 1, further comprising:
a display controller that displays, on a display, the ultrasound image representing a lesion or a region of interest in a case where the lesion or the region of interest exists.

* * * * *